(12) United States Patent
Maxik et al.

(10) Patent No.: US 9,597,420 B2
(45) Date of Patent: Mar. 21, 2017

(54) RADIATED ENERGY STERILIZATION DEVICE AND ASSOCIATED METHOD

(71) Applicant: Biological Illumination, LLC, Melbourne, FL (US)

(72) Inventors: Fredric S. Maxik, Indialantic, FL (US); David E. Bartine, Cocoa, FL (US); Robert R. Soler, Cocoa Beach, FL (US); Gregory Flickinger, Indialantic, FL (US); Ran Zhou, Rockledge, FL (US)

(73) Assignee: Biological Illumination, LLC, Cocoa Beach, FL (US)

( * ) Notice: Subject to any disclaimer, the term of this patent is extended or adjusted under 35 U.S.C. 154(b) by 86 days.

(21) Appl. No.: 14/729,719

(22) Filed: Jun. 3, 2015

(65) Prior Publication Data

US 2015/0343104 A1 Dec. 3, 2015
US 2017/0028088 A9 Feb. 2, 2017

Related U.S. Application Data

(63) Continuation-in-part of application No. 13/464,345, filed on May 4, 2012.
(Continued)

(51) Int. Cl.
*G01J 1/42* (2006.01)
*A61L 2/10* (2006.01)
(Continued)

(52) U.S. Cl.
CPC .............. *A61L 2/10* (2013.01); *A61L 2/0047* (2013.01); *A61L 9/00* (2013.01); *A61L 9/20* (2013.01); *G01J 1/42* (2013.01); *G01S 17/026* (2013.01)

(58) Field of Classification Search
CPC ... G01J 1/42; G01N 21/00; A61L 2/00; A61L 2/0047
See application file for complete search history.

(56) References Cited

U.S. PATENT DOCUMENTS 5,623,105 A 4/1997 Liston et al.
5,770,147 A 6/1998 Muller
(Continued)

FOREIGN PATENT DOCUMENTS

EP 1925709 5/2008
WO WO 2012/078476 6/2012

OTHER PUBLICATIONS

Lilienfeld, "Optical Detection of Particle Contamination on Surfaces: A Review", Pedro Lilienfeld, Aerosol Science and Technology (1986) 5:2, pp. 145-165; available online Jun. 6, 2007.*
(Continued)

*Primary Examiner* — David Porta
*Assistant Examiner* — Meenakshi Sahu
(74) *Attorney, Agent, or Firm* — Mark Malek; Daniel Pierron; Widerman Malek, PL

(57) ABSTRACT

A sterilization device comprising an ultraviolet (UV) electromagnetic radiation (EMR) emitting device, a detector configured to detect occupancy of a room associated with the sterilization device, and a controller operably connected to each of the UV EMR emitting device and the detector. The detector is configured to send a signal indicating occupancy to the controller upon a detection of occupancy. The controller is configured to operate the UV EMR emitting device to emit UV EMR only upon receiving a signal indicating no occupancy.

20 Claims, 5 Drawing Sheets

Related U.S. Application Data

(60) Provisional application No. 62/006,930, filed on Jun. 3, 2014.

(51) Int. Cl.
  *A61L 9/20*   (2006.01)
  *G01S 17/02*  (2006.01)
  *A61L 2/00*   (2006.01)
  *A61L 9/00*   (2006.01)

(56) References Cited

U.S. PATENT DOCUMENTS

| | | | |
|---|---|---|---|
| 5,859,952 | A | 1/1999 | Levin et al. |
| 6,403,030 | B1 | 6/2002 | Horton, III |
| 6,586,890 | B2 | 7/2003 | Min et al. |
| 7,270,748 | B1 | 9/2007 | Lieggi |
| 7,296,422 | B2 | 11/2007 | Strohm et al. |
| 7,419,642 | B2 | 9/2008 | Fowler et al. |
| 7,498,009 | B2 | 3/2009 | Leach et al. |
| 7,713,426 | B2 | 5/2010 | Newcombe |
| 7,862,728 | B2 | 1/2011 | Yencho |
| 8,420,022 | B2 | 4/2013 | Soler et al. |
| 8,465,172 | B2 | 6/2013 | Marson |
| 8,506,886 | B2 | 8/2013 | Owen et al. |
| 8,980,171 | B2 | 3/2015 | Mazyck et al. |
| 2005/0169795 | A1 | 8/2005 | Sanchez |
| 2009/0145855 | A1 | 6/2009 | Day et al. |
| 2009/0191100 | A1* | 7/2009 | Deal .................. A61L 2/10 422/105 |
| 2009/0208386 | A1 | 8/2009 | Barsky et al. |
| 2010/0222852 | A1* | 9/2010 | Vasily .................. A61N 5/0603 607/89 |
| 2010/0237254 | A1 | 9/2010 | Mason et al. |
| 2012/0287245 | A1* | 11/2012 | Holland .......... G08B 13/19602 348/46 |

OTHER PUBLICATIONS

U.S. Patent and Trademark Office's Final Office Action dated Dec. 31, 2015 cited in related U.S. Appl. No. 14/211,663 (21 pages).

U.S. Patent and Trademark Office's Applicant-Initiated Interview Summary dated Feb. 23, 2016 cited in related U.S. Appl. No. 14/211,663 (3 pages).

U.S. Patent and Trademark Office's Non-Final Office Action dated Jul. 23, 2014 cited in related U.S. Appl. No. 14/211,663 (17 pages).

Response to Non-Final Office Action dated Oct. 22, 2014 filed in related U.S. Appl. No. 14/211,663 (11 pages).

U.S. Patent and Trademark Office's Final Office Action dated Nov. 7, 2014 cited in related U.S. Appl. No. 14/211,663 (19 pages).

Response to Final Office Action dated Feb. 5, 2015 filed in related U.S. Appl. No. 14/211,663 (14 pages).

U.S. Patent and Trademark Office's Non-Final Office Action dated Feb. 27, 2015 cited in related U.S. Appl. No. 14/211,663 (19 pages).

Response to Non-Final Office Action dated Apr. 27, 2015 filed in related U.S. Appl. No. 14/211,663 (11 pages).

U.S. Patent and Trademark Office's Final Office Action dated May 8, 2015 cited in related U.S. Appl. No. 14/211,663 (20 pages).

Response to Final Office Action dated Aug. 7, 2015 filed in related U.S. Appl. No. 14/211,663 (12 pages).

* cited by examiner

RADIATED ENERGY STERILIZATION DEVICE AND ASSOCIATED METHOD

RELATED APPLICATIONS

This application is related to and claims benefit under 35 U.S.C. §119(e) of U.S. Provisional Patent Application Ser. No. 62/006,930 titled Radiated Energy Sterilization Device filed Jun. 3, 2014, and U.S. patent application Ser. No. 13/464,345 titled Occupancy Sensor and Associated Methods filed May 4, 2012, the content of each of which is incorporated by reference in its entirety to the extent disclosure therein is consistent with disclosure herein. This application is further related to U.S. patent application Ser. No. 14/211,663 titled Photoreactive System for Preserving Produce filed Mar. 14, 2014, the content of which is incorporated by reference in its entirety to the extent disclosure therein is consistent with disclosure herein.

FIELD OF THE INVENTION

The present invention relates to systems and methods for an electromagnetic disinfectant system. In particular, the invention relates to an ultraviolet disinfectant system which can automatically determine when to activate, and the characteristics of the activation, based on the environment.

BACKGROUND OF THE INVENTION

The use of ultraviolet (UV) electromagnetic radiation (EMR) for the purpose of disinfecting of a surface or a gaseous volume has been practiced for many years. However, such systems have not been successfully deployed into settings where the target surface for disinfection is frequently used by occupants of the space. One of the primary challenges in such an implementation is that excessive UV irradiation has many deleterious effects on such occupants. Accordingly, there is a need in the art for a system that utilizes UV EMR that can be deployed to disinfect surfaces having frequent occupancy.

This background information is provided to reveal information believed by the applicant to be of possible relevance to the present invention. No admission is necessarily intended, nor should be construed, that any of the preceding information constitutes prior art against the present invention.

SUMMARY OF THE INVENTION

With the above in mind, embodiments of the present invention are related to a sterilization device comprising an ultraviolet (UV) electromagnetic radiation (EMR) emitting device, a detector configured to detect occupancy of a room associated with the sterilization device, and a controller operably connected to each of the UV EMR emitting device and the detector. The detector may be configured to send a signal indicating occupancy to the controller upon a detection of occupancy. Additionally, the controller may be configured to operate the UV EMR emitting device to emit UV EMR only upon receiving a signal indicating no occupancy.

In some embodiments, the detector may be configured to indicate occupancy upon the detection of either of a human or a domestic animal within a field of view of the sensor. The UV EMR emitting device may be configured to emit radiation within a wavelength range from 200 nm to 300 nm. Furthermore, the UV EMR emitting device may be configured to emit radiation within a wavelength range from 260 nm to 270 nm. In some embodiments, the UV EMR emitting device is configured to emit radiation having a peak intensity at 265 nm.

The detector may be further configured to determine if a surface in a field of view thereof is contaminated. Additionally, the detector may be configured to send a signal indicating contamination of a surface to the controller upon a detection of contamination of a surface in the field of view thereof. The controller may be configured to operate the UV EMR emitting device to emit UV EMR only upon receiving both a signal indicating no occupancy and a signal indicating contamination.

In some embodiments, the sterilization device may further comprise a reservoir of dispersible titanium dioxide and a dispersing device in fluidic communication with the reservoir of dispersible titanium dioxide. The dispersing device may be configured to disperse the dispersible titanium dioxide to coat surfaces to be sterilized. Furthermore, the dispersing device may vary at least one dispersing characteristic selected from the group consisting of volume, flow rate, direction, pressure, angle of dispersion, and distance.

In some embodiments, the sterilization device may comprise a plurality of UV EMR emitting devices. At least one UV EMR emitting device of the plurality of UV EMR emitting devices may be configured to emit radiation in a primarily different direction from another UV EMR device of the plurality of UV EMR emitting devices. Furthermore, the controller may be configured to operate a first set of the plurality of UV EMR emitting devices to provide a first level of irradiation in a first direction, defined as a first UV treatment, and a second set of the plurality of UV EMR emitting devices to provide a second level of irradiation in a second direction, defined as a second UV treatment. The first level of irradiation may be different from the second level of irradiation. Additionally, the first direction may comprise an area of irradiation not comprised by the second area of irradiation. The detector may be configured to provide information to the controller regarding characteristics of the field of detection, and the controller may be configured to determine each of the first UV treatment and the second UV treatment responsive to the information received from the detector. Furthermore, the information may comprise at least one of distance to a surface, surface area, an indication of whether a surface comprises titanium dioxide, and average occupancy rate.

In some embodiments, the sterilization device may further comprise a network interface device configured to connect to a network. The network interface device may be configured to transmit indications generated by the detector across the network. Additionally, the network interface device may be configured to receive and relay to the controller information received from a remote processor across the network.

The sterilization device may further comprise a plurality of visible spectrum (VS) EMR devices configured to emit light within the visible spectrum range. The controller may be operably connected to the plurality of VS EMR devices.

DETAILED DESCRIPTION OF THE INVENTION

Figure 1:
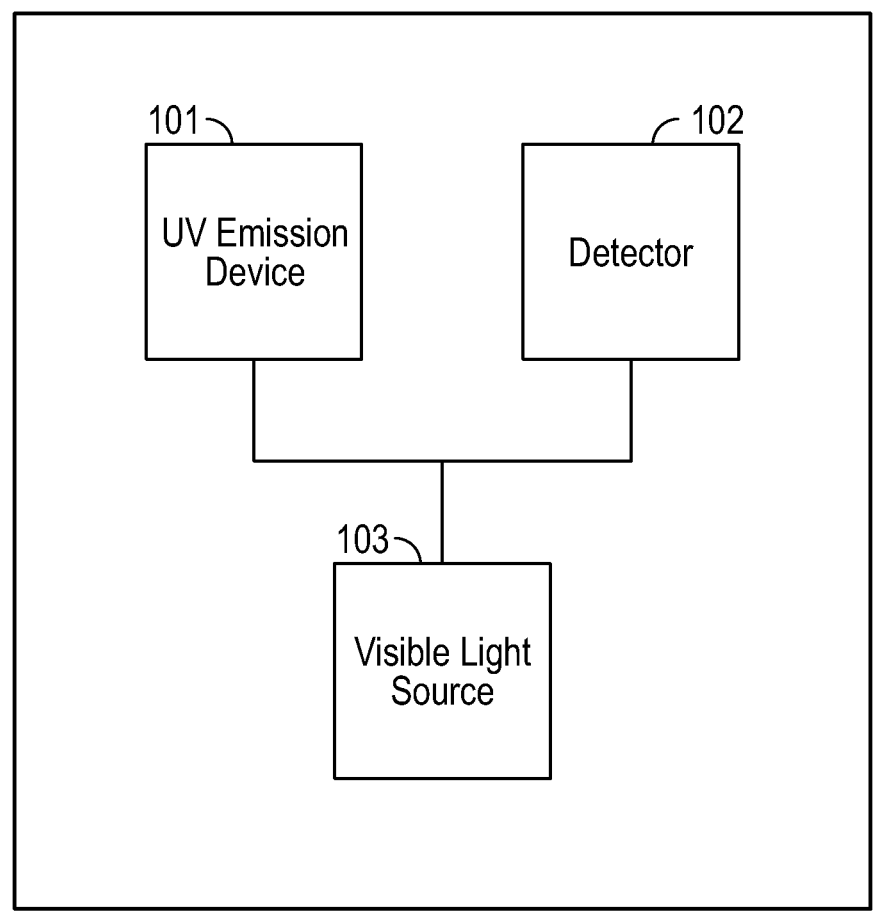
FIG. 1 illustrates an exemplary embodiment of the sterilization device of the present invention.

The present invention will now be described more fully hereinafter with reference to the accompanying drawings, in which preferred embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Those of ordinary skill in the art realize that the following descriptions of the embodiments of the present invention are illustrative and are not intended to be limiting in any way. Other embodiments of the present invention will readily suggest themselves to such skilled persons having the benefit of this disclosure. Like numbers refer to like elements throughout.

Although the following detailed description contains many specifics for the purposes of illustration, anyone of ordinary skill in the art will appreciate that many variations and alterations to the following details are within the scope of the invention. Accordingly, the following embodiments of the invention are set forth without any loss of generality to, and without imposing limitations upon, the invention.

In this detailed description of the present invention, a person skilled in the art should note that directional terms, such as "above," "below," "upper," "lower," and other like terms are used for the convenience of the reader in reference to the drawings. Also, a person skilled in the art should notice this description may contain other terminology to convey position, orientation, and direction without departing from the principles of the present invention.

Furthermore, in this detailed description, a person skilled in the art should note that quantitative qualifying terms such as "generally," "substantially," "mostly," and other terms are used, in general, to mean that the referred to object, characteristic, or quality constitutes a majority of the subject of the reference. The meaning of any of these terms is dependent upon the context within which it is used, and the meaning may be expressly modified.

Referring now to the drawings, and more particularly to FIGS. 1-5, there are shown exemplary embodiments of the method and structures according to the present invention.

Ultraviolet electromagnetic radiation (UV) can be used to sterilize objects and areas by killing microbes and breaking down undesirable substances. In addition, UV light can be applied to certain coatings to produce a sterilizing effect. For example, when UV light is applied to Titanium Dioxide ($TiO_2$), the $TiO_2$ may become a photo catalyst oxidizer and can create hydroxyl radicals and superoxide ions which can act as very strong disinfectants. While exemplary embodiments will be described in relation to $TiO_2$, other materials with similar light (EM) reactive properties can also be used.

$TiO_2$ can be applied as a coating on a given object, or may be sprayed on (e.g., a nano $TiO_2$ liquid or other $TiO_2$ liquid). $TiO_2$ is normally white in color and can have reflective properties as well. When UV light is applied to a $TiO_2$ coated or sprayed surface, the $TiO_2$ produces a sterilizing effect on the surface.

The $TiO_2$ can be utilized with broad spectrum, deep UV light and violet/near UV light. Low nm lengths may provide peak effectiveness for creating the sterilization reaction in $TiO_2$. In particular, a wavelength of 265 nm has been found to promote a peak reaction in $TiO_2$. Thus, an optimal wavelength for emissions may be in a range of 260 to 270 nm which could provide more favorable reactions with the $TiO_2$ than other UV wavelengths.

In addition, deep UV (e.g., 200-300 nm) can be applied to a surface without $TiO_2$ and still obtain a good sterilizing effect.

However, UV radiation can be potentially harmful to people and, accordingly, it may not be desirable to run UV sterilization while humans (or pets) are present. For certain areas, such as hospital bathrooms, examination rooms, operating rooms, etc., people regularly enter and leave the room causing constant contamination.

Figure 2:
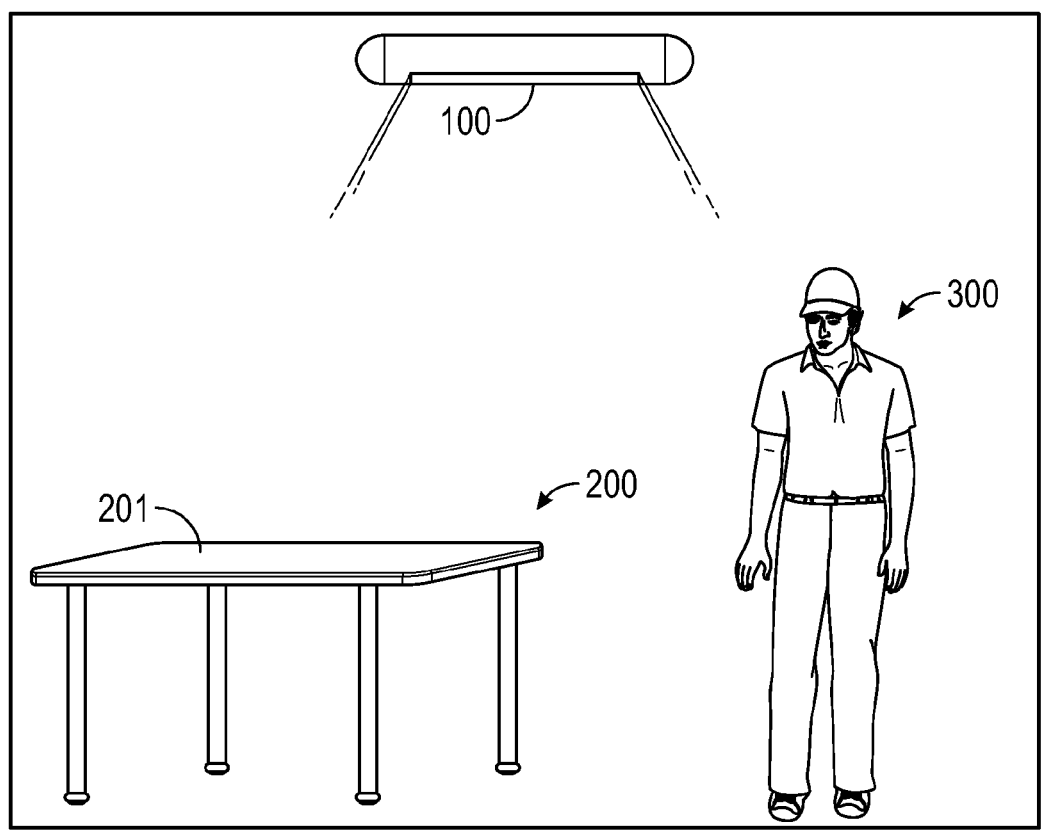
FIG. 2 illustrates a room including the sterilization device illustrated in FIG. 1.

As illustrated in FIGS. 1 and 2, in an exemplary embodiment, the sterilization device 100 may include a UV emission device 101 and a detector 102. In exemplary embodiments, the sterilization device may also include a visible light (or other light spectrum) source 103. The detector 102 may be any one or a combination of an active or passive electromagnetic emission detector (e.g., infrared detector, UV detector, etc.), camera, vibration/acoustic detector, coherent EM such as a laser, etc., which can be configured to detect when an object(s)/occupant is present in a room/area.

Thus, the sterilization device 100 can act as both a light source for the room/area, as well as perform sterilizing function when occupants are not present.

Methods and systems for detecting occupants in a room and lighting, for analyzing the characteristics of a room or area, light flight time detection, and lighting systems are described in U.S. Pat. No. 8,492,995, U.S. Pat. No. 8,515,289, and U.S. Pat. No. 8,680,457, as well as in U.S. Patent Application Publication Nos. 2013/0201290 and 2012/0287245, and also in U.S. Provisional Patent Application Ser. No. 61/936,654, the entire contents of each of which are incorporated herein by reference except to the extent disclosure therein is inconsistent with disclosure herein.

All of the aforementioned systems, and any combination or subset thereof, can be used to create a lighting device which can detect occupancy of a room (e.g., to determine if a human or pet is present or to determine a location of a human or pet in an area of detection), determine the room/area characteristics (e.g., reflectance, distance to surfaces, etc.), emit a specified EM radiation (e.g., in a particular direction based on detected people or distance to surfaces to be treated), and emit the EM for a specified time and/or at a specified intensity to sterilize/treat an environment.

The sterilization device 100 can include one or more integrated processors, to control the light source, emission devices, and detectors. Alternatively, the sterilization device 100, or group of sterilization devices 100, may be connected to a remote processor or network to provide some or all of the control and processing of data.

The detector 102 can be an array of detectors to allow mapping of the surrounding area, and may also include different type of detectors so as to allow detection of objects/occupants in general by one type and UV reflectance by another type of detector. In some embodiments, the detector 102 and the emission device 101 can be directed or formed in an array to be so as to be directed in multiple directions.

Figure 3:
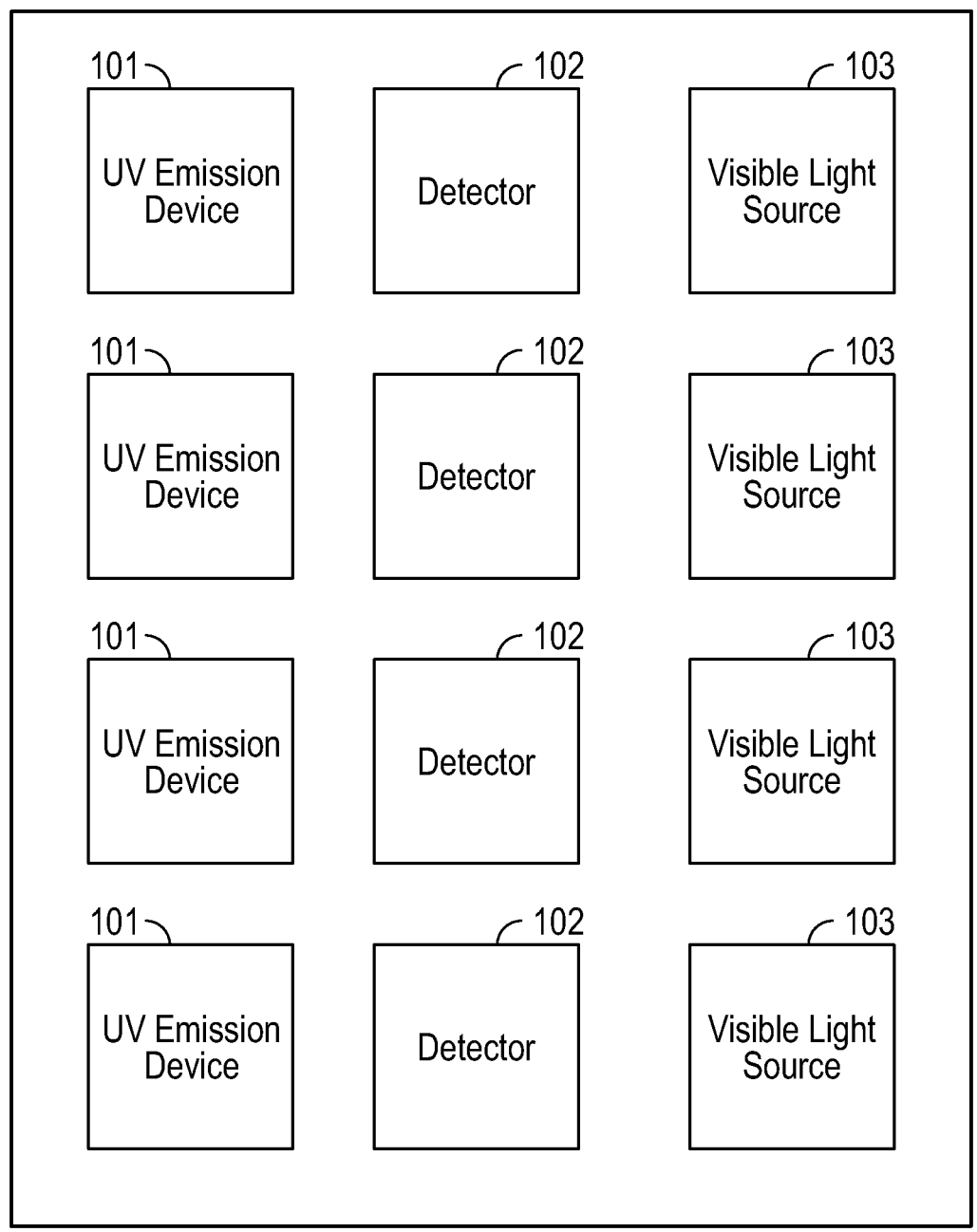
FIG. 3 illustrates an exemplary embodiment of the emission and detection array of the sterilization device illustrated in FIG. 1.

FIG. 3 illustrates an exemplary embodiment having a plurality of sensors forming detector 102. As illustrated in FIG. 3, the sterilization device 100 can include multiple UV emission devices 101, light sources 103, and detectors 102.

Figure 4A:
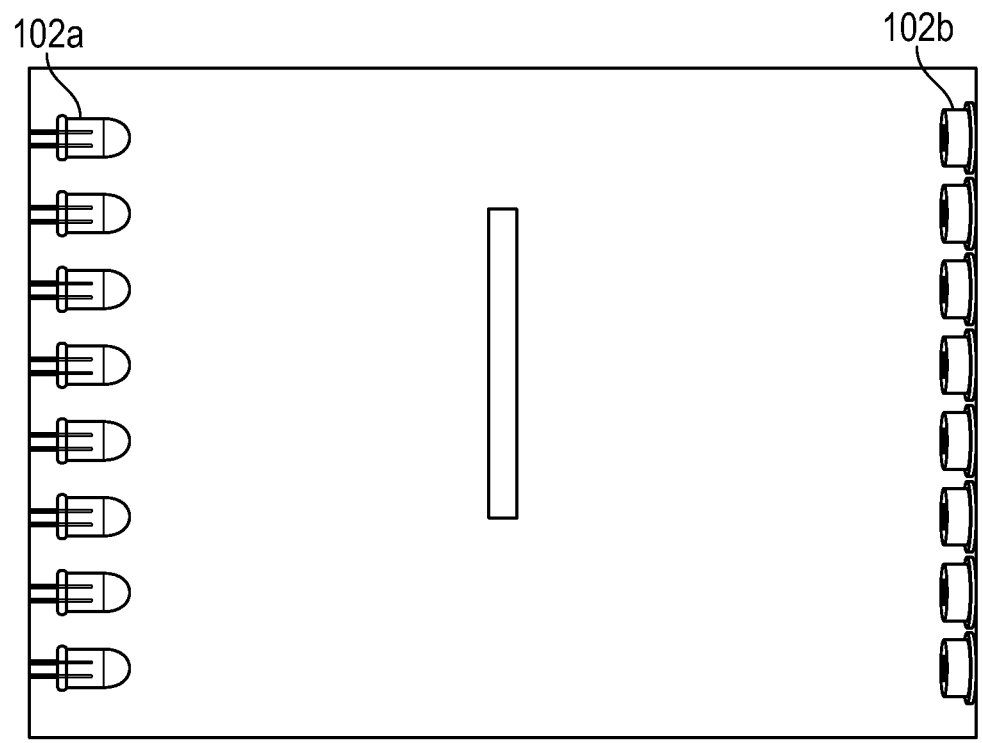
FIG. 4a illustrates an exemplary embodiment of a detector of the sterilization device illustrated in FIG. 1.

As can be seen in FIG. 4a, detectors 102 can be formed of an emitter 102a and a receiver 102b to emit and receive reflected signals. In some embodiments, some detectors 102 can emit a signal while other detectors 102 receive the emitted signals.

Figure 4B:
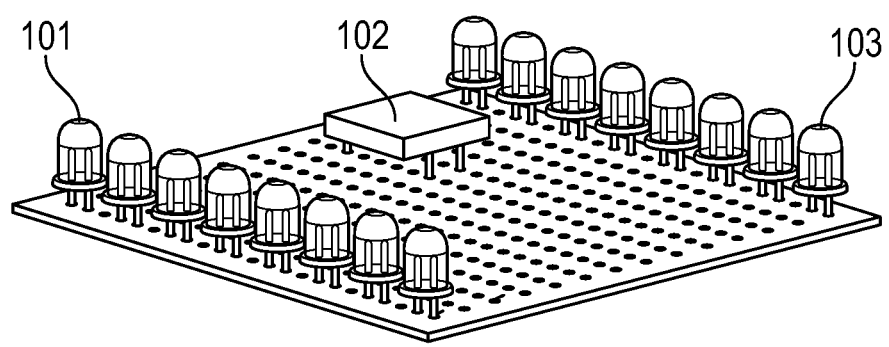
FIG. 4b illustrates an exemplary embodiment of a detector and an emitting device of the sterilization device illustrated in FIG. 1.

As illustrated in FIG. 4b, alternatively, or in addition to, in some embodiments the emission device 101 and the detector 102 can be constituted by the same LED chip. In some embodiments the light source 103 and the detector 102 can be constituted by the same LED chip. In still other embodiments, the same LED can be used for light source 103, detector 102 and emission device 101 through a use of screens (e.g., normal light screen swappable with UV emitting screen) or other emission.

In some embodiments, the same type of detector can be used to detect if an occupant is present and the characteristics of the room.

The detector 102 can also be configured to detect areas of contamination. For example, if the reflectance of a surface is detected as being faint, or of a specific wavelength, it can be determined that the surface has been contaminated by a substance. If a camera (or imaging system in general) is utilized as a detector 102, then the detector 102 can use object recognition to identify potential contaminants. In addition, detector 102 can identify contaminants based on reflected light wavelength or intensity.

In an exemplary embodiment, if a UV detector 102 is used to determine room/area characteristics, then the UV emission device 101 may provide the UV signal to be reflected and detected by the UV detector. In some embodiments, the UV detector 102 and the UV emission device 101 can be located on the same chip/die. In exemplary embodiments, the UV emission device 101, the UV detector 102, the light source 103, can all be located on the same chip/die.

In some embodiments, the sterilization device 100 can include an array of chips/dies arranged so as to emit light in primarily different directions. By so doing, the occupants and surfaces can be detected in each direction and the areas illuminated and/or sterilized in a manner tailored to the area (e.g., increased intensity for a distant surface). In some embodiments, the direction of emission of the UV emission devices 101 and/or light sources 103 can be altered (e.g., moving the LED, changing direction of emission based on refraction or reflection, etc.).

Figure 5:
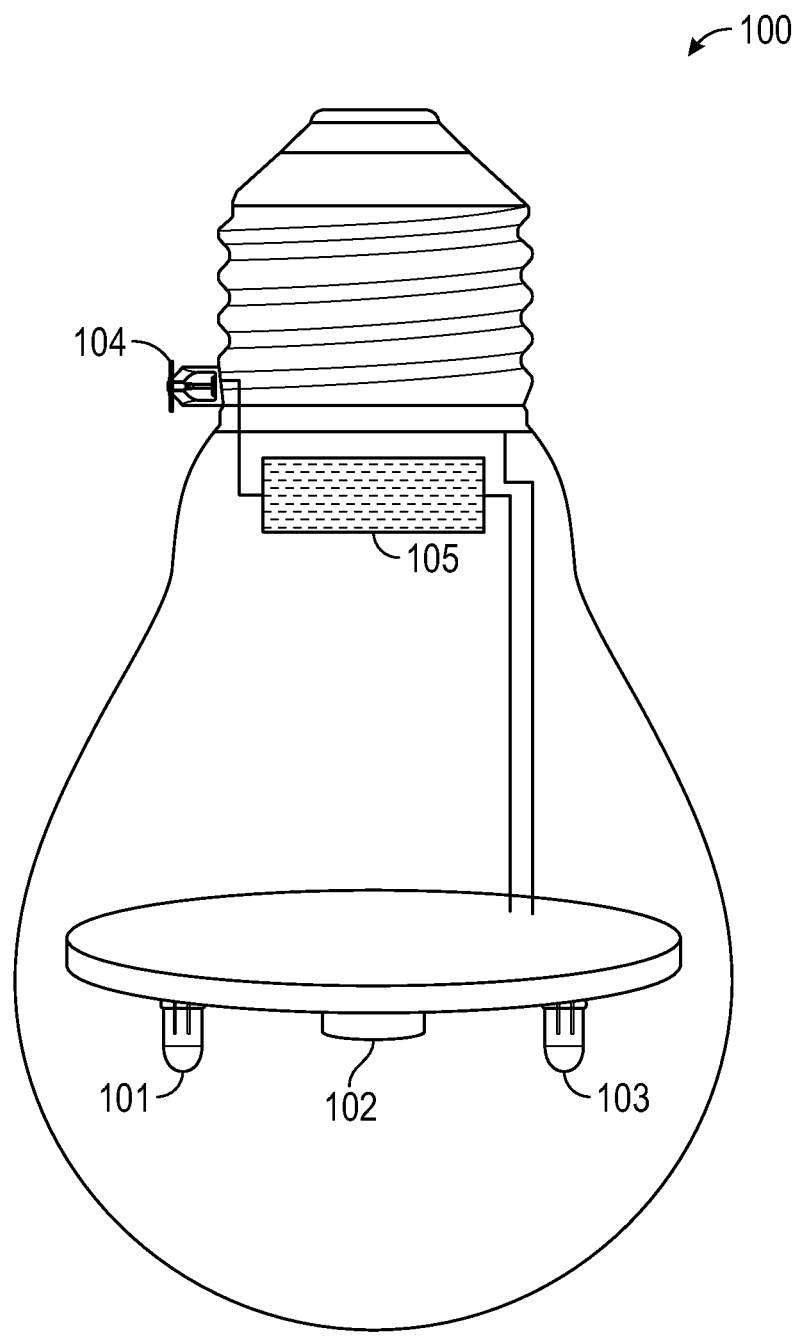
FIG. 5 illustrates an exemplary embodiment of a sterilization device including a dispersing device according to an embodiment of the present invention.

As illustrated in FIG. 5, in an exemplary embodiment, the sterilization device 100 can include a TiO2 dispersing device 104. The TiO2 dispersing device 104 may be located on, or connected to, the sterilization device 100 or may be a separate unit. The dispersing device 104 can be configured to disperse TiO2 in a fine mist or liquid so as to coat surfaces in the room to be sterilized. The dispersing device may be configured manually or automatically to vary the dispensing characteristics (e.g., volume, direction, distance/pressure, etc.). In an exemplary embodiment, the characteristics of the room detected by detector 102 can be used to control the dispensing of the TiO2. For instance, if the dispersing device includes screens, movable heads, multiple ports, or just multiple dispersing heads, then more TiO2, or TiO2 at a greater pressure/angle, can be dispersed in to an area which is further away or which the detector 102 detects as being contaminated.

The method for determining the room/area characteristics is not particularly limited. For instance, distance, reflectance, surface angle, color, etc., can be used individually or collectively to determine the room characteristics. The UV emission system 101 can then set one or more emission aspects such a direction of UV emitted, intensity, amount of time, etc. based on that information. If the duration or intensity is fixed for the entire room/area for a particular activation, then an average of the characteristics can be used, the least favorable characteristic, a mid-point, or any other method to determine the operation of the UV emission device 101.

Similarly, the dispersal device 104 can be set for different areas based on the detected characteristics. For example, a direction of TiO2 emitted, flow rate, amount of time, etc., can be based on the detected characteristics. In some embodiments, the dispersion can be done uniformly or fixed for the entire room/area for a particular activation cycle. In this case, then an average of the characteristics can be used, the least favorable characteristic, a mid-point, or any other method to determine the operation of the dispersion device 104.

In exemplary embodiments, the detector 102 can also detect the distance to the various surfaces of the room. The detector 102 can also be used to detect reflectance of the surface, angle of reflection, size of the room etc. This information can be used to determine the intensity of the UV light to be emitted and the duration of emission. This advantageously allows for the sterilization device 100 according to embodiments of the present invention to be used to automatically control dosing amounts of UV light based on the detected distance to be surface in the room to be sterilized.

In an exemplary embodiment, the sterilization device 100 serves the purpose of a normal lighting source using visible light source 103 while occupants are detected by detector 102. When there are no occupants detected in the room (or a specific area), UV emission device 101 activates. Optionally, the visible light source 103 can deactivate at this point if energy saving is desired. The detector 102 can also scan the room, either at this time or at some other previous time, to detect the dimensions of the room/area, and surface characteristics (e.g., reflectance) in order to determine the intensity of UV to emit and/or the duration to emit the UV.

In an exemplary embodiment, the UV emission device 102 may be activated whenever an occupant is not detected. When an occupant is detected by detector 102 as being in the room/area, the UV emission device 101 can be automatically deactivated. If the light source 103 is already deceived, light source 103 can optionally be activated at this point.

For example, the sterilization device 100 can be located in a room and emit UV light for a set amount of time, which can be based on the detected room characteristics, after occupants are no longer detected in the room. When occupants are detected in the room, the UV light deactivates and the normal light activates.

The UV emission device 101 and the light source 103 are not particularly limited. For instance, the UV emission device 101 and light source 103 may be light emitting diodes (LEDs) and may be formed on separate or the same dies. The light source 103 and UV emission device 101 could also be fluorescent or any other suitable source. Similarly, the light source 103 and UV emission device 101 can comprise multiple sources or LEDs and have the ability to be directed to certain areas of the room by activating or deactivating certain LED, screening, etc.

In exemplary embodiments, the UV emission device 101 can be activated or directed so as to create a controlled area of effect. This can allow certain areas of the room to receive more UV of more intensity or longer duration than other areas. For example, the LEDs primarily illuminating a certain area (e.g., an area beneath the fixture, an area not directly under the fixture, etc.) can be activated longer or driven individually or as a group so as to create a greater intensity.

In some embodiments, the increased or decreased UV exposure can be determined based on the room/area characteristics detected by detector 102. For example, in an exemplary embodiment, the distance to the surface of a countertop is detected or set. When an occupant leaves, the UV emission device emits UV for a time period based on the distance to the surface of the countertop surface, the intensity with which light emitted by the UV emission device irradiates the countertop surface, and a minimum dosage that must be achieve in order to accomplish a selected level of sterilization. In some embodiments, a maximum distance may be determined for the room/area detected by the detector 102, from which a minimum UV illumination time may be determined so as to reach the minimum required dosage. The UV emission device may emit UV for at least the minimum UV illumination time.

When a person or domestic animal enters the room, the UV emission device deactivates and normal light is emitted from the light source 103. The amount of time for UV emission can be reset at the next cycle, or if a certain amount of time has passed, the cycle can restart without resetting the UV exposure time. Optionally, at some point in the process, such as when occupants are not present, the dispensing device 104 can spray TiO2 on the surfaces. Application of TiO2 can be based on time, amount of motion detected, contamination detected, etc.

In another example, the UV emission device can emit deep UV to clean the surfaces based on the room characteristics. When an occupant is detected as entering the room, the UV emission device 101 can switch off UV emission, switch to violet/low UV, or can control the shape/direction of the emitted deep UV so that the occupant is not targeted or may do any combination of these things based on preset setting or detected occupants and room characteristics. The method of shaping the deep UV emission is not particularly limited and can be done through shielding, selectively activating UV emission devices 101, etc.

While the above description contains much specificity, these should not be construed as limitations on the scope of any embodiment, but as exemplifications of the presented embodiments thereof. Many other ramifications and variations are possible within the teachings of the various embodiments. While the invention has been described with reference to exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best or only mode contemplated for carrying out this invention, but that the invention will include all embodiments falling within the scope of the described invention. Also, in the drawings and the description, there have been disclosed exemplary embodiments of the invention and, although specific terms may have been employed, they are unless otherwise stated used in a generic and descriptive sense only and not for purposes of limitation, the scope of the invention therefore not being so limited. Moreover, the use of the terms first, second, etc. do not denote any order or importance, but rather the terms first, second, etc. are used to distinguish one element from another. Furthermore, the use of the terms a, an, etc. do not denote a limitation of quantity, but rather denote the presence of at least one of the referenced item.

What is claimed is:

1. A sterilization device comprising:
    an ultraviolet (UV) electromagnetic radiation (EMR) emitting device;
    a detector configured to detect occupancy of a room associated with the sterilization device; and
    a controller operably connected to each of the UV EMR emitting device and the detector;
    wherein the detector is configured to send a signal indicating occupancy to the controller upon a detection of occupancy; and
    wherein the controller is configured to operate the UV EMR emitting device to emit UV EMR upon receiving a signal indicating no occupancy.

2. The sterilization device according to claim 1 wherein the detector is configured to indicate occupancy upon the detection of either of a human or a domestic animal within a field of view of the sensor.

3. The sterilization device according to claim 1 wherein the UV EMR emitting device is configured to emit radiation within a wavelength range from 200 nm to 300 nm.

4. The sterilization device according to claim 3 wherein the UV EMR emitting device is configured to emit radiation within a wavelength range from 260 nm to 270 nm.

5. The sterilization device according to claim 1 wherein the UV EMR emitting device is configured to emit radiation having a peak intensity at 265 nm.

6. The sterilization device according to claim 1 wherein the detector is further configured to determine if a surface in a field of view thereof is contaminated.

7. The sterilization device according to claim 6 wherein:
    the detector is configured to send a signal indicating contamination of a surface to the controller upon a detection of contamination of a surface in the field of view thereof; and
    the controller is configured to operate the UV EMR emitting device to emit UV EMR upon receiving both a signal indicating no occupancy and a signal indicating contamination.

8. The sterilization device according to claim 1 further comprising:
    a reservoir of dispersible titanium dioxide; and
    a dispersing device in fluidic communication with the reservoir of dispersible titanium dioxide;
    wherein the dispersing device is configured to disperse the dispersible titanium dioxide to coat surfaces to be sterilized.

9. The sterilization device according to claim 8 wherein the dispersing device may vary at least one dispersing characteristic selected from the group consisting of volume, flow rate, direction, pressure, angle of dispersion, and distance.

10. The sterilization device according to claim 1 comprising a plurality of UV EMR emitting devices; wherein at least one UV EMR emitting device of the plurality of UV EMR emitting devices is configured to emit radiation in a primarily different direction from another UV EMR device of the plurality of UV EMR emitting devices.

11. The sterilization device according to claim 10 wherein:
the controller is configured to operate a first set of the plurality of UV EMR emitting devices to provide a first level of irradiation in a first direction, defined as a first UV treatment, and a second set of the plurality of UV EMR emitting devices to provide a second level of irradiation in a second direction, defined as a second UV treatment;
wherein the first level of irradiation is different from the second level of irradiation; and
wherein the first direction comprises an area of irradiation not comprised by the second area of irradiation.

12. The sterilization device according to claim 11 wherein:
the detector is configured to provide information to the controller regarding characteristics of the field of detection; and
the controller is configured to determine each of the first UV treatment and the second UV treatment responsive to the information received from the detector.

13. The sterilization device according to claim 12 wherein the information comprises at least one of distance to a surface, surface area, an indication of whether a surface comprises titanium dioxide, and average occupancy rate.

14. The sterilization device according to claim 1 further comprising a network interface device configured to connect to a network; wherein the network interface device is configured to transmit indications generated by the detector across the network; and wherein the network interface device is configured to receive and relay to the controller information received from a remote processor across the network.

15. The sterilization device according to claim 1 further comprising a plurality of visible spectrum (VS) EMR devices configured to emit light within the visible spectrum range; wherein the controller is operably connected to the plurality of VS EMR devices.

16. A sterilization device comprising:
an ultraviolet (UV) electromagnetic radiation (EMR) emitting device configured to emit radiation within a wavelength range from 200 nm to 300 nm;
a detector configured to detect occupancy of a room associated with the sterilization device; and
a controller operably connected to each of the UV EMR emitting device and the detector;
wherein the detector is configured to provide information to the controller regarding characteristics of the field of detection;
wherein the controller is configured to determine a UV treatment responsive to the information received from the detector;
wherein the detector is configured to send a signal indicating occupancy to the controller upon a detection of occupancy and to send a signal indicating no occupancy upon not detecting occupancy;
wherein the detector is further configured to determine if a surface in a field of view thereof is contaminated by a substance and to send a signal indicating contamination of a surface to the controller upon a detection of contamination of a surface in the field of view thereof; and
wherein the controller is configured to operate the UV EMR emitting device to emit UV EMR upon receiving both a signal indicating no occupancy and a signal indicating contamination.

17. The sterilization device according to claim 16 wherein:
the detector is configured to provide information to the controller regarding characteristics of the field of detection;
the controller is configured to operate the UV EMR emitting device responsive to the information received from the detector; and
the information comprises at least one of distance to a surface, surface area, an indication of whether a surface comprises titanium dioxide, and average occupancy rate.

18. The sterilization device according to claim 17 further comprising:
a reservoir of dispersible titanium dioxide; and
a dispersing device connected to the reservoir of dispersible titanium dioxide;
wherein the dispersing device is configured to disperse the dispersible titanium dioxide to coat surfaces to be sterilized.

19. The sterilization device according to claim 18 wherein:
the controller is operatively coupled to the dispersing device; and
the controller is configured to operate the dispersing device responsive to the information received from the detector.

20. A sterilization device comprising:
a plurality of ultraviolet (UV) electromagnetic radiation (EMR) emitting devices;
a detector configured to detect occupancy of a room associated with the sterilization device; and
a controller operably connected to each of the UV EMR emitting device and the detector;
wherein the detector is configured to send a signal indicating occupancy to the controller upon a detection of occupancy and to send a signal indicating no occupancy upon not detecting occupancy;
wherein the controller is configured to operate the UV EMR emitting device to emit UV EMR upon receiving a signal indicating no occupancy; and
wherein the detector is configured to provide information to the controller regarding characteristics of the field of detection;
wherein at least one UV EMR emitting device of the plurality of UV EMR emitting devices is configured to emit radiation in a primarily different direction from another UV EMR device of the plurality of UV EMR emitting devices; and
wherein the controller is configured to operate the plurality of UV EMR emitting devices responsive to the information received from the detector.

* * * * *